United States Patent [19]

Fürst et al.

[11] Patent Number: 4,492,797
[45] Date of Patent: Jan. 8, 1985

[54] DEA-STEROIDS

[75] Inventors: Andor Fürst, Basel; Peter Keller, Reinach; Marcel Müller, Frenkendorf, all of Switzerland

[73] Assignee: Hoffmann-La Roche Inc., Nutley, N.J.

[21] Appl. No.: 432,503

[22] Filed: Oct. 4, 1982

Related U.S. Application Data

[63] Continuation of Ser. No. 121,614, Feb. 14, 1980, abandoned.

[30] Foreign Application Priority Data

Feb. 23, 1979 [CH] Switzerland .......................... 1838/79
Jan. 10, 1980 [CH] Switzerland ............................ 172/80

[51] Int. Cl.$^3$ ............................................ C07D 307/94
[52] U.S. Cl. ..................................... 549/265; 424/279
[58] Field of Search ................ 549/265; 424/279, 317; 562/499

[56] References Cited

U.S. PATENT DOCUMENTS

| | | | |
|---|---|---|---|
| 2,971,009 | 2/1961 | Burtner | 549/265 |
| 3,766,213 | 10/1973 | Fürst et al. | 549/265 |
| 3,766,256 | 10/1973 | Uskokovic | 549/265 |
| 3,920,703 | 11/1975 | Alig et al. | 549/265 |
| 4,119,627 | 10/1978 | Wieland | 549/265 |
| 4,140,700 | 2/1979 | Fürst | 549/265 |

Primary Examiner—Norma S. Milestone
Attorney, Agent, or Firm—Jon S. Saxe; Bernard S. Leon; Matthew Boxer

[57] ABSTRACT

The present disclosure is directed to 5-oxo- or methylene 17β-hydroxy saturated or unsaturated deA-steroids wherein the 17α-position contains a propionic acid or propanol substituent and derivatives thereof wherein the hydroxy group at the 17-position forms a lactone ring with the carboxy substituent when the substituent at position 21 is carboxy. The deA-steroids and derivatives of the present disclosure are useful as potassium-sparing diuretics or for flushing oedemas.

5 Claims, No Drawings

DEA-STEROIDS

This is a continuation of application Ser. No. 121,614 filed Feb. 14, 1980, now abandoned.

BACKGROUND OF THE INVENTION

The present invention relates to novel deA-steroids, a process for their manufacture and pharmaceutical preparations thereof.

SUMMARY OF THE INVENTION

The present invention provides deA-steroids of the general formula

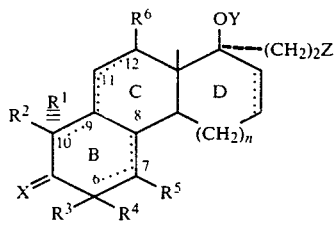

wherein $R^1$ and $R^2$ each are hydrogen or lower alkyl; $R^3$ is hydrogen, halogen or methyl; $R^4$ is hydrogen or, where $R^3$ is methyl, $R^4$ is hydrogen or methyl; $R^5$ is hydrogen, cyano, lower alkoxy, aryl-(lower alkoxy) or $SR^7$; or $R^3$ and $R^5$ together are methylene; $R^6$ is hydrogen or acylthio; $R^7$ is acyl, alkyl or aralkyl; X is oxo or methylene; Y is hydrogen; Z is hydroxymethyl or —COA; A is hydroxy; or Y and A together are an O—C bond; n is zero or 1 and the dotted bonds within the rings are optional; with the provisos that (a) each ring contains at most one double bond;
(b) the B-ring is 9(10)-unsaturated when the C-ring is 11(12)-unsaturated;
(c) at least one of $R^5$ and $R^6$ is hydrogen;
(d) $R^5$ is hydrogen when $R^4$ is methyl;
(e) $R^5$ is hydrogen or $R^3$ and $R^5$ together are methylene and $R^6$ is hydrogen when Z is carboxy;
(f) $R^3$ is hydrogen, halogen or methyl and $R^4$ is absent when a 6(7)- or 7(8)-double bond is present;
(g) the 6(7)- and 11(12)-bonds are saturated when $R^6$ is acylthio; and
(h) $R^1$ is absent and $R^2$ is lower alkyl when a 9(10)-double bond is present, the C and D rings are saturated, n is zero and Z is —COA, and salts thereof where Z is carboxy.

DETAILED DESCRIPTION OF THE INVENTION

As used herein, the term "alkyl" means straight- or branched-chain saturated aliphatic hydrocarbon groups preferably containing 1-8 carbon atoms. Representative of such groups are methyl, ethyl, isopropyl, butyl, pentyl, hexyl and the like.

The term "cycloaliphatic" means a lower alkyl hydrocarbon group which is closed to form a ring structure. Preferred cycloaliphatic groups are saturated lower alkyl hydrocarbon ring structures containing from 3–6 carbon atoms. Especially-preferred are saturated groups containing 4–6 carbon atoms.

The term "alkoxy" means a lower alkyl group attached to the remainder of the molecule by oxygen. Examples of alkoxy are methoxy, ethoxy, propoxy, isopropoxy and the like.

The term "aryl" means an organic, aromatic radical derived by the removal of one atom (e.g., phenyl) which can be substituted or unsubstituted by one or more lower alkyl groups (e.g., tolyl).

The term "aralkyl" means a group in which an alkyl atom is substituted by an aryl group wherein aryl and alkyl are as defined above. Examples of aralkyl are benzyl and phenethyl.

The term "acyl" means the residue from the removal of the hydroxy group from a lower alkanoic carboxylic acid. Examples of such acids are formic acid, acetic acid, pivalic acid, propionic acid, butyric acid, caproic acid, oenanthic acid, undecylenic acid and oleic acid. Preferred acyl groups are $C_{1-7}$ alkanoyl groups, especially acetyl. Also within the definition of acyl are groups derived from the removal of a hydroxy group from a cycloaliphatic lower alkanoic carboxylic acid. Representative of such acids are cyclopentyl propionic acid, cyclohexyl propionic acid and the like. Also within the definition of acyl are groups derived from the removal of the hydroxy groups from a substituted or unsubstituted aromatic carboxylic acid preferably containing 7–15 carbon atoms (e.g., benzoic acid, phenyl acetic acid).

The salts of the deA-steroids of formula I may be any pharmaceutically-acceptable salt, in particular, alkali metal salts (e.g. sodium and potassium salts), ammonium salts and alkaline earth metal salts (e.g. calcium salts). The potassium salts are preferred.

A preferred class of deA-steroids of formula I comprises those of the formula

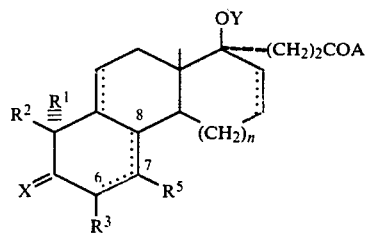

wherein $R^1$, $R^2$, $R^3$, $R^5$, A, X, Y, n and the dotted bonds are as above. Also preferred are deA-steroids of formula I or I-1 in which the B- and C-rings are unsaturated. A further preferred group of deA-steroids of formula I comprises those in which Z is hydroxymethyl. DeA-steroids of formulae I and I-1 in which at least one of $R^1$ and $R^2$ is lower alkyl are also preferred.

In the deA-steroids of formula I in which the carbon atoms in the 6- and 7-positions are not associated with double bonds, the substituents $R^3$, $R^4$ and $R^5$ can have the α- or β-configuration. 6α- and 7α-substituted deA-steroids are preferred.

The deA-steroids of formula I can be manufactured in accordance with the invention by (a) oxidizing the group denoted by $OR^8$ in a compound of the formula

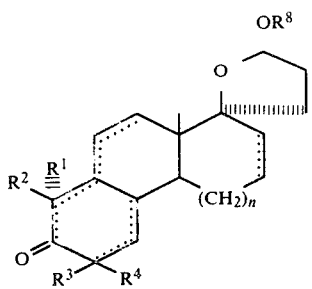

to the oxo group, or (b) dehydrogenating a compound of the formula

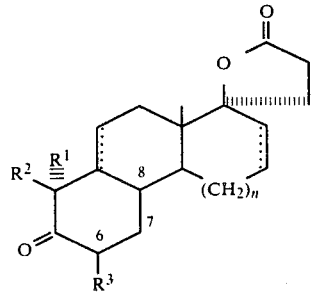

or the corresponding acid or a salt thereof in the 6(7)- or 7(8)-position, or (c) halogenating a compound of the formula

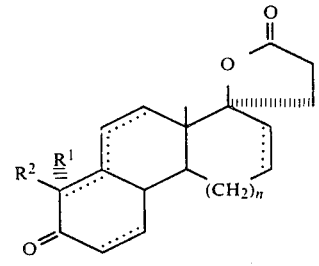

or the corresponding acid or a salt thereof, or (d) reacting a compound of the formula

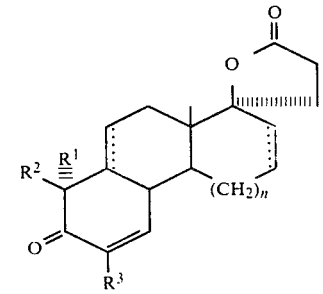

or

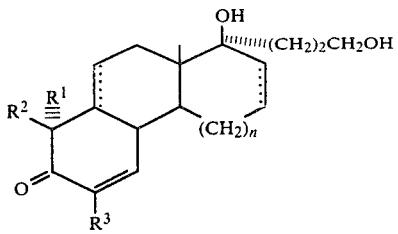

with a compound of the formula R$^7$SH, a lower alkanol, an aryl-(lower alkanol) or hydrogen cyanide, or (e) reacting a compound of the formula

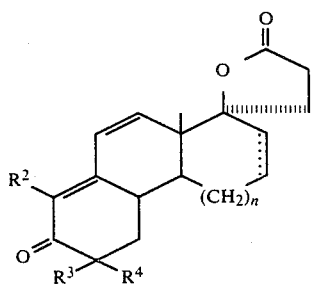

or

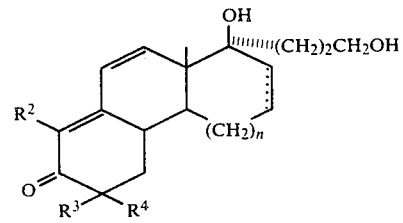

with a compound of the formula R$^6$SH, or (f) adding a methylene group at the 6(7)-double bond present in a compound of the formula

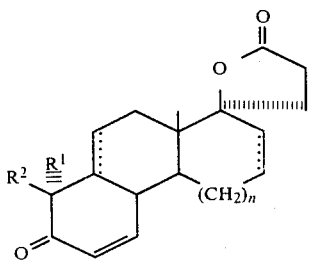

or in the corresponding acid or salt thereof, or (g) reacting a compound of the formula

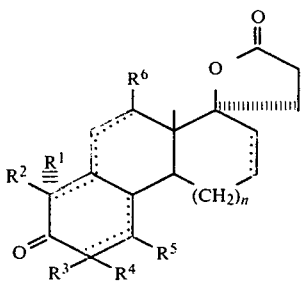

or the corresponding acid or a salt thereof with a methylene-phosphonium compound under the conditions of a Wittig reaction, or (h) opening the lactone ring in a compound of the formula

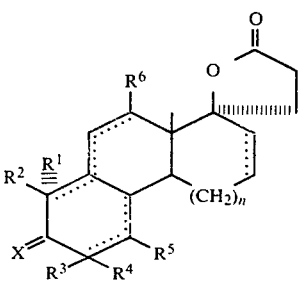

or (i) reducing a deA-steroid of formula I in which Z is —COA to give a corresponding deA-steroid in which Z is hydroxymethyl, whereby in the foregoing formulae $R^1$, $R^2$, $R^3$, $R^4$, $R^5$, $R^6$, $R^7$, X, n and the dotted bonds are as above and $R^8$ is hydrogen or alkyl.

The oxidation in accordance with embodiment (a) of the process can be carried out with a chromic oxidizing agent, especially $CrO_3/H_2SO_4$ (Jones' reagent). The oxidation is generally carried out at a temperature up to room temperature. When a compound of formula II in which $R^8$ is alkyl (e.g. methyl) is used, it is convenient to carry out the oxidation at a higher temperature (e.g. at 50° C.).

The dehydrogenation in accordance with embodiment (b) of the process is preferably carried out in a manner known per se by halogenation, especially bromination, followed by dehydrohalogenation (dehydrobromination). The bromination can be carried out using a brominating agent such as bromine or pyridinium hydrobromide/perbromide and the dehydrohalogenation can be carried out using a base such as collidine, pyridine or lithium bromide/lithium carbonate/dimethylformamide. The dehydrogenation can also be carried out directly, for example using an oxidizing agent such as dichlorodicyanobenzoquinone or chloranil.

The dehydrogenation according to the preceding paragraph yields a 6(7)-unsaturated deA-steroid of formula I. A 7(8)-unsaturated deA-steroid of formula I can be obtained therefrom by deconjugation of the 6(7)-double bond, for example by converting the 6(7)-unsaturated deA-steroid into a 3-enol ether (e.g. by treatment with orthoformic acid ester/p-toluenesulphonic acid) and careful saponification of the latter, for example with a weak acid such as formic acid or acetic acid at a low temperature (e.g. at 0° C.)

The halogenation of a compound of formula Ib in accordance with embodiment (c) of the process can be carried out in a manner known per se; for example, by reaction with a halogenating agent such as a N-chloroamide or imide (e.g. N-chlorosuccinimide) or with elemental chlorine [see J. Am. Chem. 72, 4534 (1950)], or by converting a compound of formula Ib into a 3-enol ester or 3-enol ether (e.g. the 3-enol acetate) and then reacting the 3-enol ester or 3-enol ether with chlorine [See J. Am. Chem. Soc. 82, 1230 (1960)], with a N-chloroimide [see J. Am. Chem. Soc. 82, 1230 (1960); 77, 3827 (1955)] or with perchloryl fluoride [see J. Am. Chem. Soc. 81, 5259 (1959); Chem. and Ind. 1959, 1317]. Furthermore, trifluoromethylhypofluorite can be used as the fluorinating agent.

The introduction of a substituent $R^5$ into a compound of formula Ic or Id in accordance with embodiment (d) of the process can be carried out in a manner known per se by reaction with a compound of the formula $R^5SH$ such as a mercaptan (e.g. methyl mercaptan or ethyl mercaptan) or a thiocarboxylic acid (e.g. thioacetic acid) or with a corresponding alcohol (e.g. methanol or benzyl alcohol). The reaction can be carried out in an inert solvent such as an ether (e.g. dioxan or tetrahydrofuran), an alcohol (e.g. methanol or ethanol) or a hydrocarbon (e.g. chloroform). However, the reagent (e.g. the thiocarboxylic acid) is conveniently used in excess and can thereby serve as the solvent. The hydrogen cyanide which is used to introduce a cyano group is conveniently generated in situ (e.g. from a cyanohydrin such as acetone cyanohydrin).

The introduction of a substituent $R^6$ into a compound of formula Ie or If in accordance with embodiment (e) of the process can be carried out in a manner analogous to that described earlier in connection with embodiment (d) by treatment with a thiocarboxylic acid (e.g. thioacetic acid).

The methylenation in accordance with embodiment (f) of the process can be carried out in a manner known per se; for example, using trimethylsulphoxonium iodide in the presence of a base such as sodium hydride or potassium tert.butylate in an aprotic dipolar solvent such as dimethyl sulphoxide, tetrahydrofuran, hexamethylphosphoric acid triamide, dimethylformamide or mixtures thereof at a temperature between about 0° C. and 50° C., conveniently at room temperature.

The Wittig reaction in accordance with embodiment (g) of the process is carried out in a manner known per se in the presence of a strong base (e.g. butyl lithium, sodium hydride, potassium tert.butylate or the sodium salt of dimethyl sulphoxide) in a solvent (e.g. an ether such as tetrahydrofuran).

The cleavage of the lactone ring in accordance with embodiment (h) of the process can be carried out in a manner known per se; for example using a base such as potassium hydroxide or sodium hydroxide in a solvent, for example an optionally aqueous alcohol .such as (aqueous) methanol, ethanol or isopropanol, at a temperature between about 0° C. and the reflux temperature of the mixture, conveniently at about 50° C. The thus-obtained salts, which correspond to the base used, can be converted by acidification (e.g. using hydrochloric acid, into the free acids. The latter can be converted into salts by treatment with suitable bases.

The reduction in accordance with embodiment (i) of the process can be carried out in a manner which is known for the reduction of lactones to alcohols; for example, using a complex metal hydride such as lithium aluminium hydride.

The starting materials of formula II can be prepared as follows: A compound of the formula

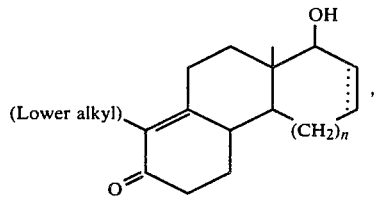

III wherein n and the dotted bond are as above, such as methylcycloketol (lower alkyl=methyl, n=zero, double bond absent) is reductively alkylated with a lower alkyl iodide such as methyl iodide [see J.A.C.S. 89, 54–64 (1967)]. Thereafter, the oxo group is ketalized, the hydroxy group is oxidized to a 17-oxo group and the product is reacted with the lithium derivative of 3-bromopropionaldehyde dimethyl acetal. Thereafter, the dimethyl acetal group and the ketal group attached to the ring are hydrolyzed. There is thus obtained a compound of formula II in which $R^1$ and $R^2$ each is lower alkyl and in which the 9(11)-position (steroid nomenclature) is saturated. Corresponding 9(11)-unsaturated compounds of formula II can be prepared as follows: A compound of formula III is converted into a tert.butyl ether and this is treated with a lower alkyl iodide (e.g. methyl iodide in tert.butanol in the presence of potassium tert.butylate) to give compounds of formula IV and V.

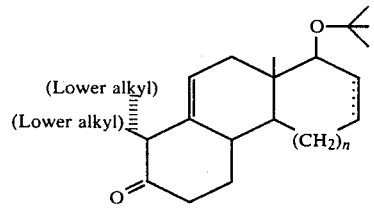

IV

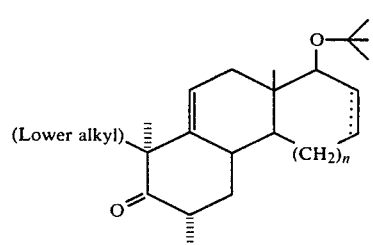

V wherein n and the dotted bond are as above.

After cleavage of the tert.butyl ether, the oxo group attached to the ring is ketalized and the spirolactone group is built up in the manner described earlier. Compounds of formula II with $R^1$ and $R^2$ each is hydrogen can be prepared from compounds of the general formula

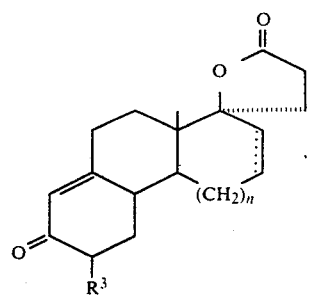

VI wherein $R^3$, n and the dotted bond are as above, by hydrogenating the conjugated double bond (e.g. using palladium/hydrogen) followed by optional 6(7)-dehydrogenation which can be carried out in an analogous manner to that described in connection with embodiment (b) of the process.

Compounds of formula II in which $R^3$ and $R^4$ each is methyl can be prepared from compounds of formula IV, V or VI by methylation using methyl iodide in the presence of lithium diisopropylamide in a manner known per se.

A double bond can be introduced in the 11(12)-position of a corresponding 11(12)-saturated starting material (e.g. a compound of formula II in which the C-ring is saturated) by treatment with a dehydrogenating agent such as chloranil in a manner known per se. Moreover, the starting materials can be prepared as described in the Examples or in analogy thereto.

The compounds of formula I and their salts can be used as pharmaceuticals. Inter alia, they have diuretic activity and are suitable for blocking the action of aldosterone or of desoxycorticosterone acetate. They can accordingly be used, for example, as potassium-sparing diuretics or for flushing oedemas.

The aldosterone-antagonistic activity was determined using the following experimental procedure: Female Holtzman rats (150–180 g) were bilaterally adrenalectomised 70–74 hours before the experiment. After the operation, the rats received 0.9% sodium chloride solution as drinking water and commercial dry feed. The feed was removed 16–17 hours before the experiment, whereas the sodium chloride solution remained available ad libitum. The sodium and potassium in the urine were determined by flame-photometry. The test substances were dissolved in 0.3% sodium chloride solution and administered in an amount of 30 ml/kg by means of a stomach probe. Each experiment was accompanied by a control group which was treated similarly but which received in place of the test substances the same volumes of pure sodium chloride solution. 30 minutes later aldosterone was injected subcutaneously. 120 minutes after administering the test substances the urinary bladders of the rats were emptied by slight suprapubic pressure. The rats were placed in metabolic cages without access to feed and water. The urine was collected every 3 hours and the urinary bladders were pressed out at the end of the experiment. The spontaneous urine and the residual urine were pooled. The results are summarized in the following Table (urea volumes V, $Na^+$ and $K^+$ in % of the control group).

| Test substance | Dosage [mg/kg] | V | $Na^+$ | $K^+$ |
|---|---|---|---|---|
| A | 10 | 119 | 220 | 99 |

-continued

| | | | | |
|---|---|---|---|---|
| B | 10 | 118 | 217 | 86 |
| | 0.1 | 118 | 122 | 127 |
| C | 10 | 163 | 289 | 101 |
| | 3 | 125 | 202 | 108 |
| | 1 | 118 | 204 | 118 |
| D | 10 | 144 | 246 | 118 |
| | 1 | 179 | 244 | 127 |
| E | 10 | 136 | 284 | 89 |
| | 1 | 171 | 415 | 118 |
| F | 10 | 172 | 200 | 114 |
| | 3 | 132 | 219 | 100 |
| | 1 | 122 | 274 | 103 |
| G | 10 | 93 | 224 | 96 |
| | 1 | 126 | 244 | 99 |
| H | 0.1 | 135 | 213 | 76 |
| I | 10 | 108 | 158 | 85 |
| | 1 | 158 | 293 | 121 |
| J | 10 | 154 | 272 | 107 |
| K | 10 | 153 | 226 | 98 |
| | 1 | 136 | 171 | 114 |
| L | 10 | 114 | 289 | 84 |
| | 1 | 113 | 220 | 116 |
| M | 10 | 113 | 254 | 55 |
| | 1 | 106 | 245 | 108 |
| N | 1 | 114 | 224 | 75 |
| | 0.1 | 158 | 297 | 86 |

A: 5-Oxo-A-tetranor-10α,17a-pregn-6-ene-21,17-carbolactone
B: 7α-(Acetylthio)-5-oxo-5,10-seco-A-tetranor-10α,17a-pregnane-21,17-carbolactone
C: Potassium 17-hydroxy-5-oxo-5,10-seco-A-tetranor-10α,17a-pregn-6-ene-21-carboxylate
D: 5-Oxo-1,5-seco-A-trinor-17α-pregnane-21,17-carbolactone
E: 7α-(Acetylthio)-5-oxo-1,5-seco-A-trinor-17α-pregnane-21,17-carbolactone
F: Potassium 17-hydroxy-5-oxo-1,5-seco-A-trinor-17α-pregn-6-ene-21-carboxylate
G: 6-Bromo-5-oxo-1,5-seco-A-trinor-17α-pregn-6-ene-21,17-carbolactone
H: 5-Oxo-A-tetranor-17α-pregna-9,11-diene-21,17-carbolactone
I: 7α-(Ethylthio)-5-oxo-1,5-seco-A-trinor-17α-pregnane-21,17-carbolactone
J: 7α-Cyano-5-oxo-1,5-seco-A-trinor-17α-pregnane-21,17-carbolactone
K: Potassium 17-hydroxy-5-oxo-1,5-seco-A-trinor-17α-pregna-6,9,(11)-diene-21-carboxylate
L: 6α-Methyl-5-oxo-1,5-seco-A-trinor-17α-pregn-9(11)ene-21,17-carbolactone
M: 7α-(Acetylthio)-5-oxo-3,5-seco-A-nor-10α,17a-pregnane 21,17-carbolactone
N: 6,6-Dimethyl-5-oxo-1-5-seco-A-trinor-17α-pregn-9(11)-ene-21,17-carbolactone The compounds of formula I and their salts can be used as medicaments; for example, in the form of pharmaceutical preparations which contain them in association with a compatible pharmaceutical carrier material. This carrier material can be an organic or inorganic inert carrier material suitable for enteral or parenteral administration such as, for example, water, gelatin, gum arabic, lactose, starch, magnesium stearate, talc, vegetable oils, polyalkyleneglycols, petroleum jelly etc. The pharmaceutical preparations can be made up in a solid form (e.g. as tablets, dragées, suppositories or capsules) or in a liquid form (e.g. as solutions, suspensions or emulsions). The pharmaceutical preparations may be sterilized and/or may contain adjuvants such as preserving, stabilizing, wetting or emulsifying agents, salts for varying the osmotic pressure or buffers. They can also contain still other therapeutically valuable substances.

The medicaments can be produced in a manner known per se by mixing a compound of formula I or a salt thereof with a non-toxic, inert, solid and/or liquid carrier material customary per se in such preparations and suitable for therapeutic administration (e.g. the aforementioned carrier materials) and, if desired, bringing the mixture into the desired dosage form. The compounds of formula I and their salts can suitably be administered to adults in a dosage of about 0.1–10 mg/kg per day.

The following Examples illustrate the process provided by the present invention:

EXAMPLE 1

A solution of 22.9 g of 2-carboxyethyl-triphenylphosphonium perbromide in 125 ml of terahydrofuran is added dropwise within 20 minutes to a solution of 9.6 g of 5-oxo-1,5-seco-A-trinor-17α-pregna-21,17-carbolactone in 100 ml of tetrahydrofuran. After stirring at room temperature for 2 hours, the mixture is poured into ice/water and extracted with methylene chloride. The crude product obtained by working-up the methylene chloride extract is boiled for 1 hour under argon with a mixture of 105 ml of dimethylformamide, 10.5 g of lithium bromide and 10.5 g of lithium carbonate. The cooled solution is poured into water and extracted with ether/methylene chloride (4:1). By chromatography of the residue obtained from the extract on silica gel with toluene/ethyl acetate (7:3) there is obtained as the main product 5-oxo-1,5-seco-A-trinor-17α-pregn-6-ene-21,17-carbolactone of melting point 128°–129° C. (from diethyl ether); $[\alpha]_D^{25} = 112.5°$ (dioxan, c=0.2).

As the byproduct there is obtained 6-bromo-5-oxo-1,5-seco-A-trinor-17α-pregn-6-ene-21,17-carbolactone of melting point 194°–195° C. (from diethyl ether/methylene chloride); $[\alpha]_D^{25} = -38°$ (dioxan, c=0.2).

EXAMPLE 2

In analogy to Example 1, from 5-oxo-1,5-seco-A-trinor-17α-pregn-9(11)-ene-21,17-carbolactone there is obtained 5-oxo-1,5-seco-A-trinor-17α-pregna-6,9(11)-diene-21,17-carbolactone of melting point 195°–197° C.; $[\alpha]_D^{25} = -292°$ (dioxan, c=0.5).

As the byproduct there can be isolated 5-oxo-1,5-seco-A-trinor-17α-pregna-7,9(11)-diene-21,17-carbolactone of melting point 159°–160° C.; $[\alpha]_D^{25} = +40.5$ (dioxan, c=0.2).

EXAMPLE 3

In analogy to Example 1, from 5-oxo-3,5-seco-A-nor-17α-pregna-21,17-carbolactone there is obtained 5-oxo-3,5-seco-A-nor-17α-pregn-6-ene-21,17-carbolactone of melting point 181°–183° C.; $[\alpha]_D^{25} = -92.5°$ (dioxan, c=1.0).

As the byproduct there is obtained 6-bromo-5-oxo-3,5-seco-A-nor-17α-pregn-6-ene-21,17-carbolactone of melting point 194°–196° C.; $[\alpha]_D^{25} = -40.1°$ (dioxan, c=1.0).

EXAMPLE 4

In analogy to Example 1, from 5-oxo-2,5-seco-A-dinor-17α-pregnane-21,17-carbolactone there is obtained 5-oxo-2,5-seco-A-dinor-17α-pregn-6-ene-21,17-carbolactone of melting point 157°–159° C.; $[\alpha]_D^{25} = -101.3°$ (dioxan, c=1.0).

As the byproduct there is obtained 6-bromo-5-oxo-2,5-seco-A-dinor-17α-pregn-6-ene-21,17-carbolactone of melting point 194°–196° C.; $[\alpha]_D^{25} = -48°$ (dioxan, c=1.0).

EXAMPLE 5

In analogy to Example 1, from 6-methyl-5-oxo-1,5-seco-A-trinor-17α-pregnane-21,17-carbolactone there is obtained 6-methyl-5-oxo-1,5-seco-A-trinor-17α-pregn-6-ene-21,17-carbolactone of melting point 181°–182° C.; $[\alpha]_D^{25} = -86°$ (dioxan, c=0.5).

EXAMPLE 6

In analogy to Example 1, from 6-methyl-5-oxo-1,5-seco-A-trinor-17α-pregn-9(11)-ene-21,17-carbolactone there is obtained 6-methyl-5-oxo-1,5-seco-A-trinor-17α-pregna-6,9(11)-diene-21,17-carbolactone of melting point 195°–198° C.; $[\alpha]_D^{25} = -256.4°$ (dioxan, c=0.5).

EXAMPLE 7

In analogy to Example 1, from 5-oxo-3,5-seco-A-nor-10α,17α-pregnane-21,17-carbolactone there is obtained 5-oxo-3,5-seco-A-nor-10α,17α-pregn-6-ene-21,17-carbolactone of melting point 149°–150° C.; $[\alpha]_D^{25} = -119.2°$ (dioxan, c=0.5).

As the byproduct there is obtained 6-bromo-5-oxo-3,5-seco-A-nor-10α,17α-pregn-6-ene-21,17-carbolactone of melting point 179°–180° C.

The 5-oxo-3,5-seco-A-nor-10α,17α-pregnane-21,17-carbolactone used as the starting material is prepared as follows:

Methylcycloketol is reductively alkylated with n-propyl iodide to give 17β-hydroxy-3,5-seco-A-nor-10α-androstan-5-one of melting point 117°–118.5° C. which is ketalised to give 17β-hydroxy-3,5-seco-A-nor-10α-androstan-5-one ethylene acetal of melting point 153°–154° C. Oxidation of this ketal with pyridinium chlorochromate yields 3,5-seco-A-nor-10α-androstane-5,17-dione 5-(ethylene acetal) [$[\alpha]_D = -108°$ (dioxan, c=0.36)] from which there is obtained in analogy to example 41 5-oxo-3,5-seco-A-nor-10α,17α-pregnane-21,17-carbolactone of melting point 150°–151° C.

EXAMPLE 8

6 g of 5-oxo-5,10-seco-A-tetranor-10α,17α-pregnane-21,17-carbolactone are dissolved in 900 ml of ether and the solution is cooled to ca 3° C. in an ice-bath. The solution is treated dropwise while stirring within 10 minutes with a solution of 3368 mg of bromine in 12.42 ml of acetic acid. Sodium sulphite solution is added to the practically colourless solution and the mixture is subsequently extracted with diethyl ether. After evaporation of the extract, there are obtained 8.62 g of a colourless oil which is boiled for 1 hour under argon with a suspension of 6 g of lithium carbonate and 6 g of lithium bromide. After working-up the mixture and chromatography of the residue on silica gel with toluene/ethyl acetate (9:1), there is obtained 5-oxo-A-tetranor-10α,17α-pregn-6-ene-21,17-carbolactone.

EXAMPLE 9

5.6 ml of sulphuryl chloride are added within 5 minutes to a solution, cooled to 15° C., of 10 g of 5-oxo-1,5-seco-A-trinor-17α-pregn-6-ene-21,17-carbolactone in 330 ml of pyridine. The solution is held at 15° C. for 1 hour, then poured into ice-water and extracted with ether. The ethereal extract is washed with dilute hydrochloric acid and water, dried over sodium sulphate and evaporated under reduced pressure. The residue is chromatographed on 800 g of silica gel. Elution with toluene/ethyl acetate (95:5) yields 1.8 g of pure 6-chloro-5-oxo-1,5-seco-A-trinor-17α-pregn-6-ene-21,17-carbolactone of melting point 220°–223° C. (from acetone/hexane): $[\alpha]_D^{25} = -57.2°$ (dioxan, c=1.0).

EXAMPLE 10

658 mg of 6-bromo-5-oxo-1,5-seco-A-trinor-17α-pregn-6-ene-21,17-carbolactone are suspended in a mixture of 10 ml of methanol and 2.15 ml of water. 2.15 ml of thioacetic acid are added to this suspension under argon. After 3 hours, the mixture is diluted with water. The residue is filtered off under suction, dried and crystallized twice from acetone. There is obtained 7α-(acetylthio)-6α-bromo-5-oxo-1,5-seco-A-trinor-17α-pregnane-21,17-carbolactone of melting point 178°–181° C. (decomposition); $(\alpha)_D^{25} = -18.4°$ (dioxan, c=0.5).

EXAMPLE 11

520 mg of 6-bromo-5-oxo-1,5-seco-A-trinor 17α-pregn-6-ene-21,17-carbolactone are dissolved in 15 ml of isopropanol. The solution is treated with 0.68 l of 2N potassium hydroxide and the mixture is left to stand under an argon atmosphere for 2 hours. After evaporation of the mixture, there is obtained potassium 6-bromo-17-hydroxy-5-oxo-1,5-seco-A-trinor-17α-pregn-6-ene-21-carboxylate in the form of a strongly hygroscopic foam; $[\alpha]_D^{25} = -55.5°$ (ethanol, c=0.2).

EXAMPLE 12

In analogy to Example 11, from 6-chloro-5-oxo-1,5-seco-A-trinor-17α-pregn-6-ene-21,17-carbolactone there is obtained potassium 6-chloro-17-hydroxy-5-oxo-1,5-seco-A-trinor-17α-pregn-6-ene-21-carboxylate in the form of an amorphous substance; $[\alpha]_D^{25} = -67.1°$ (methanol, c=1.0).

EXAMPLE 13

4.4 g of trimethylsulphoxonium iodide and 0.82 g of sodium hydride dispersion (50% in mineral oil) are treated under an argon atmosphere at ca 15° C. with 15 ml of dimethyl sulphoxide. After stirring at room temperature for 2 hours the mixture is treated with a solution of 3.02 g of 5-oxo-1,5-seco-A-trinor-17α-pregn-6-ene-21,17-carbolactone in 15 ml of dimethyl sulphoxide. The mixture is stirred overnight at room temperature under argon and then treated dropwise at 10° C. with 10 ml of glacial acetic acid. The mixture is then poured into water and extracted with ether. The extract is washed, dried and evaporated. The residue is chromatographed on silica gel with hexane/ether (2:1) and, after crystallization from methylene chloride/diethyl ether/hexane, yields pure 6,7-dihydro-5-oxo-3'H-cyclopropa[6,7]-1,5-seco-A-trinor-17α-pregn-6-ene-21,17-carbolactone in two diastereomeric forms. One isomer (probably the 6β,7β-dihydro form) has a melting point of 214°–216° C.; $[\alpha]_D^{25} = -105°$ (dioxan, c=0.5). The other isomer (probably the 6α,7α-dihydro form) melts at 178°–179° C.; $[\alpha]_D^{25} = -113°$ (dioxan, c=0.2).

EXAMPLE 14

5.64 ml of 2N potassium hydroxide are added to a solution of 5-oxo-1,5-seco-A-trinor-17α-pregn-6-ene-21,17-carbolactone in 123 ml of isopropanol. The mixture is stirred at room temperature for 2 hours under argon. For the working-up, about 70% of the isopropanol is distilled off and, after cooling, the potassium 17-hydroxy-5-oxo-1,5-seco-A-trinor-17α-pregn-6-ene-21-carboxylate crytallizes out in the form of colourless

EXAMPLE 15

In analogy to Example 14, from 5-oxo-1,5-seco-A-trinor-17α-pregna-6,9(11)-diene-21,17-carbolactone there is obtained potassium 17-hydroxy-5-oxo-1,5-seco-A-trinor-17α-pregna-6,9(11)-diene-21-carboxylate which melts from 110° C. (beginning of decomposition); $[\alpha]_D^{25} = -242°$ (ethanol, c=0.2).

EXAMPLE 16

In analogy to Example 14, from 6-methyl-5-oxo-1,5-seco-A-trinor-17α-pregn-6-ene-21,17-carbolactone there is obtained potassium 17-hydroxy-6-methyl-5-oxo-1,5-seco-A-trinor-17α-pregn-6-ene-21-carboxylate as a strongly hygroscopic foam of melting point 265°–268° C. (decomposition); $[\alpha]_D^{25} = -96°$ (ethanol, c=0.5).

EXAMPLE 17

In analogy to Example 14, from 6-methyl-5-oxo-1,5-seco-A-trinor-17α-pregna-6,9(11)-diene-21,-17-carbolactone there is obtained potassium 17-hydroxy-6-methyl-5-oxo-1,5-seco-A-trinor-17α-pregna-6,9(11)-diene-21-carboxylate of melting point 160°–165° C.; $[\alpha]_D^{25} = -230.5°$ (ethanol, c=0.2).

EXAMPLE 18

In analogy to Example 14, from 5-oxo-3,5-seco-A-nor-10α-17α-pregn-6-ene-21,17-carbolactone there is obtained potassium 17-hydroxy-5-oxo-3,5-seco-A-nor-10α,17α-pregn-6-ene-21-carboxylate of melting point 256°–260° C.; $[\alpha]_D^{25} = -121.4°$ (ethanol, c=0.5).

EXAMPLE 19

In analogy to Example 14, from 5-oxo-A-tetranor-10α,17α-pregn-6-ene-21,17-carbolactone there is obtained potassium 17-hydroxy-5-oxo-A-tetranor-10α-17α-pregn-6-ene-21-carboxylate of melting point 225°–230° C. (decomposition). $[\alpha]_D^{25} = -102°$ (dioxan, c=0.2).

EXAMPLE 20

In analogy to Example 14, from 6,7-dihydro-5-oxo-3'H-cyclopropa[6,7]-1,5-seco-A-trinor-17α-pregn-6-ene-21,17-carbolactone there is obtained potassium 6,7-dihydro-17-hydroxy-5-oxo-3'H-cyclopropa[6,7]-1,5-seco-A-trinor-17α-pregn-6-ene-21-carboxylate of melting point 265°–267° C.; $[\alpha]_D^{25} = -86°$ (dioxan, c=0.5).

EXAMPLE 21

In analogy to Example 14, from 5-oxo-3,5-seco-A-nor-17α-pregn-6-ene-21,17-carbolactone there is obtained potassium 17-hydroxy-5-oxo-3,5-seco-A-nor-17α-pregn-6-ene-21-carboxylate in the form of an amorphous substance; $[\alpha]_D^{25} = -86.4°$ (methanol, c=1).

EXAMPLE 22

5 g of 5-oxo-1,5-seco-A-trinor-17α-pregn-6-ene-21,17-carbolactone are suspended in 20.5 ml of methanol and 4.4 ml of water. The suspension is treated dropwise during 10 minutes under argon with 4.4 ml of thioacetic acid. After stirring at room temperature for 3 hours, starting material can no longer be detected on a thin-layer chromatogram. The solution is then poured into ice/water and the precipitate is filtered off under suction and recrystallized from methanol/water. There is obtained 7α-(acetylthio)-5-oxo-1,5-seco-A-trinor-17α-pregnane-21,17-carbolactone of melting point 147°–148° C. $[\alpha]_D^{25} = -27°$ (dioxan, c=0.2).

EXAMPLE 23

In analogy to Example 22, from 5-oxo-1,5-seco-A-trinor-17α-pregna-6,9(11)-diene-21,17-carbolactone there is obtained 7α-(acetylthio)-5-oxo-1,5-seco-A-trinor-17α-pregn-9(11)-ene-21,17-carbolactone of melting point 153°–154° C.; $[\alpha]_D^{25} = -113°$ (dioxan, c=0.2); and 7β-(acetylthio)-5-oxo-1,5-seco-A-trinor-17α-pregn-9(11-ene-21,17-carbolactone of melting point 158°–162° C.; $[\alpha]_D^{25} = -84.5°$ (dioxan, c=0.2).

EXAMPLE 24

In analogy to Example 22, from 6-methyl-5-oxo-1,5-seco-A-trinor-17α-pregn-6-ene-21,17-carbolactone there is obtained, after chromatography of the product on silica gel with hexane/ethyl acetate (4:1), 7α-(acetylthio)-6α-methyl-5-oxo-1,5-seco-A-trinor-17α-pregnane-21,17-carbolactone of melting point 203°–205° C.; $[\alpha]_D^{25} = 0°$ (dioxan, c=0.2).

EXAMPLE 25

In analogy to the Example 22, from 6-methyl-5-oxo-1,5-seco-A-trinor-17α-pregna-6,9(11)-diene-21,17-carbolactone there is obtained 7α-(acetylthio)-6α-methyl-5-oxo-1,5-seco-A-trinor-17α-pregn-9(11)-ene-21,17-carbolactone of melting point 207°–210° C.; $[\alpha]_D^{25} = -7.5°$ (dioxan, c=0.2).

EXAMPLE 26

In analogy to Example 22, from 5-oxo-3,5-seco-A-nor-10α-17α-pregn-6-ene-21,17-carbolactone there is obtained 7α-(acetylthio)-5-oxo-3,5-seco-A-nor-10α,1-7α-pregnane-21,17-carbolactone of melting point 168°–169° C.; $[\alpha]_D^{25} = -18°$ (dioxan, c=0.5).

The 7β-isomer can be isolated from the mother liquors.

EXAMPLE 27

In analogy to Example 22, from 5-oxo-A-tetranor-10α-17α-pregn-6-ene-21,17-carbolactone there is obtained 7α-(acetylthio)-5-oxo-A-tetranor-10α,17α-pregnane-21,17-carbolactone.

EXAMPLE 28

In analogy to Example 22, from 5-oxo-3,5-seco-A-nor-17α-pregn-6-ene-21,17-carbolactone there is obtained 7α-(acetylthio)-5-oxo-3,5-seco-A-nor-17α-pregnane-21,17-carbolactone of melting point 162°–165° C.; $[\alpha]_D^{25} = -17.2°$ (dioxan, c=1).

EXAMPLE 29

In analogy to Example 22, from 5-oxo-2,5-seco-A-dinor-17α-pregn-6-ene-21,17-carbolactone there is obtained 7α-(acetylthio)-5-oxo-2,5-seco-A-dinor-17α-pregnane-21,17-carbolactone of melting point 194°–196° C.; $[\alpha]_D^{25} = -9°$ (dioxan, c=1).

EXAMPLE 30

In analogy to Example 22, from 6-chloro-5-oxo-1,5-seco-A-trinor-17α-pregn-6-ene-21,17-carbolactone there is obtained 7α-(acetylthio)-6α-chloro-5-oxo-1,5-seco-A-trinor-17α-pregnane-21,17-carbolactone of melting point 204°–209° C.; $[\alpha]_D^{25} = -17.3°$.

EXAMPLE 31

In analogy to Example 22, from 5-oxo-1,5-seco-A-trinor-17α-pregn-6-ene-21,17-carbolactone and thiopropionic acid there is obtained 7α-(propionylthio)-5-oxo-1,5-seco-A-trinor-17α-pregnane-21,17-carbolactone of melting point 148°–149° C.; $[\alpha]_D^{25} = -31.1°$.

EXAMPLE 32

A solution of 3.02 g of 5-oxo-1,5-seco-A-trinor-17α-pregn-6-ene-21,17-carbolactone in 20 ml of ethyl mercaptan and 2 ml of piperidine is held at room temperature for 90 minutes. For the working-up, the solvent is removed by evaporation under reduced pressure and the residue is recrystallized from acetone/hexane. There are obtained 2.9 g of pure 7α-(ethylthio)-5-oxo-1,5-seco-A-trinor-17α-pregnane-21,17-carbolactone of melting point 180°–181° C.; $[\alpha]_D^{25} = -51.9°$ (dioxan, c=1.0)

EXAMPLE 33

2 ml of saturated sodium carbonate solution and 1.3 ml of acetone cyanohydrin are added to a solution of 2 g of 5 oxo-1,5-seco-A-trinor-17α-pregn-6-ene-21,17-carbolactone in 40 ml of methanol and 4 ml of tetrahydrofuran. The mixture is heated to reflux for 2 hours while stirring. For the working-up, the solution is cooled, poured into ice/water and extracted with ether. The ethereal extract yields 2.2 g of colourless crystals which, after chromatography on silica gel and crystallization from acetone/hexane, give pure 7α-cyano-5-oxo-1,5-seco-A-trinor-17α-pregnane-21,17-carbolactone of melting point 240°–241° C.; $[\alpha]_D^{25} = -5.7°$ (dioxan, c=1.0)

EXAMPLE 34

5-Oxo-1,5-seco-A-trinor-17α-pregna-21,17-carbolactone is reacted with 2.2 mol equivalents of bromine in analogy to Example 1. After working-up as described in Example 1, 6-bromo-5-oxo-1,5-seco-A-trinor-17α-pregn-6-ene-21,17-carbolactone is obtained as the main product.

EXAMPLE 35

1500 mg of 5-oxo-1,5-seco-A-trinor-17α-pregn-6-ene-21,17-carbolactone are heated to reflux for 7 days under argon in a mixture of 30 ml of methanol and 4 ml of aqueous 2N sodium hydroxide. The mixture is then diluted with water, acidified with 2N hydrochloric acid and extracted with ether/methylene chloride (4:1). The organic phases are washed with sodium chloride solution, dried over magnesium sulphate and evaporated under reduced pressure. The residue is chromatographed on a 100-fold amount of silica gel with toluene-/ethyl acetate (19:1). As a non-polar product there is firstly isolated 5-oxo-1,5-seco-A-trinor-17α-pregn-7-ene-21,17-carbolactone which, after crystallization from acetone/hexane, melts at 153°–157° C.; $[\alpha]_D = 8.5°$ (dioxan, c=0.2). From the subsequent fractions there are obtained unreacted starting material, 7α-methoxy-5-oxo-1,5-sec-A-trinor-17α-pregnane-21,17-carbolactone of melting point 138°–142° C. (from ether); $[\alpha]_D = -12.5°$ (dioxan, c=0.2); as well as 7-methoxy-5-oxo-1,5-seco-A-trimor-17α-pregn-6-ene-21,17-carbolactone of melting point 167°–169° C. (from methylene chloride/ether); $[\alpha]_D = -63°$ (dioxan, c=0.2).

EXAMPLE 36

2 g of 5-oxo-A-tetranor-17α-pregna-9,11-diene-21,17-carbolactone are dissolved in 40 ml of isopropanol, the solution is treated with 3.42 ml of 2N potassium hydroxide solution and the mixture is stirred for 1 hour in an argon atmosphere. Subsequently, the solution is concentrated with the repeated addition of isopropanol (azeotropic removal of water) and, while stirring vigorously, treated with a 6-fold amount of acetone, whereupon the potassium salt precipitates. After cooling overnight at +5° C., the potassium salt is filtered off under suction and immediately dried at 80° C. in a high vacuum. There are thus obtained 1.83 g of potassium 17-hydroxy-5-oxo-A-tetranor-17α-pregna-9,11-diene-21-carboxylate which sinters at 169° C. (subsequent foam formation); $[\alpha]_D = -113.4°$ (ethanol, c=0.5); UV: $\lambda_{max} = 292$ nm, $\epsilon = 24950$.

In an analogous manner there is obtained sodium 17-hydroxy-5-oxo-A-tetranor-17α-pregna-9,11-diene-21-carboxylate; $[\alpha]_D = -118°$ (ethanol, c=0.5); UV: $\lambda_{max} = 293$ nm, $\epsilon = 22600$.

EXAMPLE 37

2.6 g of 5-oxo-A-tetranor-17α-pregn-9-ene-21,17-carbolactone are dissolved in 39 ml of tert.butanol and, together with 2.6 g of chloranil, boiled at reflux for 5 hours in an argon atmosphere. The cooled product is poured into ice/water and extracted with ether. The organic phases are washed twice with 0.1N sodium hydroxide and then with sodium chloride solution until they are neutral. The thus-obtained crude product is chromatographed on a 100-fold amount of silica gel with hexane/ethyl acetate (2:1). The crude product is crystallized from acetone/diisopropyl ether. There is thus obtained 5-oxo-A-tetranor-17α-pregna-9,11-diene-21,17-carbolactone of melting point 122°–123° C.; $[\alpha]_D^{25} = -211°$ (dioxan, c=0.2); UV: $\lambda_{max} = 289$ nm, $\epsilon = 26200$.

In an analogous manner, from 5-oxo-1,2,3,4,19-pentanor-17α-pregn-9-ene-21,17-carbolactone there is obtained 5-oxo-1,2,3,4,19-pentanor-17α-pregna-9,11-diene-21,17-carbolactone of melting point 153°–154° C. (from methylene chloride/ether); UV: $\lambda_{max} = 180$ nm, $\epsilon = 27000$; $[\alpha]_D = -234°$ (dioxan, c=0.5).

EXAMPLE 38

433 mg of 5-oxo-A-tetranor-17α-pregna-9,11-diene-21,17-carbolactone are dissolved in 8.7 ml of isopropanol and 8.7 ml of water. 56.4 mg of calcium hydroxide are added to the solution. The mixture is stirred at 50° C. in an argon atmosphere for 2 hours and is then concentrated with the repeated addition of isopropanol. After the addition of ethyl acetate, the product is filtered off under suction and dried. There are thus obtained 386 mg of calcium 17-hydroxy-5-oxo-A-tetranor-17α-pregna-9-11-diene-21-carboxylate.

EXAMPLE 39

300 mg of lithium aluminium hydride are suspended in 37.9 ml of tetrahydrofuran. Thereto there is added dropwise a solution of 1.6 g of 5-oxo-A-tetranor-17α-pregna-9,11-diene-21,17-carbolactone in 46 ml of tetrahydrofuran and subsequently the mixture is boiled at reflux for 1 hour under argon. While cooling there are added 2.5 ml of ethyl acetate and subsequently 50 ml of 0.5N hydrochloric acid. After working-up the mixture, there are obtained 1.5 g of crude 5,17β-dihydroxy-17-(3-hydroxypropyl)-A-tetranorandrosta-9,11-diene.

1.1 g of the thus-obtained crude product are suspended, together with 1.38 g of dichlorodicyanoquinone, in 45.8 ml of dioxan and the mixture is stirred at room temperature under argon for 48 hours. For the working-up, the mixture is poured into ice/water and extracted with ether. The extracts are washed with sodium bicarbonate solution and subsequently with sodium chloride solution until they are neutral. The thus-obtained crude product is chromatographed on silica gel with hexane/toluene (1:1) and finally with toluene. Crystallization from methylene chloride/hexane yields 400 mg of 17β-hydroxy-17-(3-hydroxypropyl)-A-tetranorandrosta-9,11-dien-5-one in the form of yellowish crystals of melting point 168°–169° C.; $[\alpha]_D = -170°$ (dioxan, c=0.2); UV: $\lambda_{max} = 292$ nm, $\epsilon = 26000$.

EXAMPLE 40

610 mg of 5-oxo-A-tetranor-17α-pregna-9,11,diene-21,17-carbolactone in 5 ml of thioacetic acid are refluxed under argon for 5 hours. For the working-up, the mixture is poured into ice/water and extracted with ether. The organic phase is washed with 1N potassium hydroxide solution and then with water until neutral. After drying over magnesium sulphate and evaporation, the crude product is chromatographed on 150 g of silica gel with toluene/ethyl acetate. The fractions which are eluted first contain unreacted starting material. From the following fractions there are obtained 36 mg of pure 12β-(acetylthio)-5-oxo-A-tetranor-17α-pregn-9-ene-21,17-carbolactone of melting point 195°–198° C. (after crystallization from acetone/isopropanol); $[\alpha]_D = -45°$ (dioxan).

EXAMPLE 41

10 g of 1,5-seco-A-trinorandrostane-5,17-dione 5-(ethylene acetal) are dissolved in 168 ml of tetrahydrofuran and the solution is cooled to −20° C. There are now added 2.35 g of finely cut lithium wire and subsequently 36.5 g of 3-bromopropionaldehyde dimethyl acetal are added dropwise within 2 hours. The cooling bath is now removed and the mixture is stirred for a further 1 hour, the temperature rising to room temperature. The unconsumed lithium is filtered off, the solution is poured into ice/water and extracted with ether which has been washed with sodium chloride solution. The combined extracts are dried over magnesium sulphate and concentrated on a rotary evaporator. There are thus obtained 20 g of a reddish oil which is processed without further purification.

The foregoing oily product is dissolved in 143 ml of glacial acetic acid, 47 ml of water and 5 g of p-toluenesulphonic acid are added and the mixture is stirred overnight. For the working-up, the mixture is poured into ice/water and extracted with ether which has been washed with sodium carbonate solution and finally with water until neutral. After drying and evaporation, there are obtained 12 g of a red-brown oil which is processed without further purification.

The whole of the crude product obtained is dissolved in 61 ml of acetone and 37 ml of dichloromethane and oxidized with an excess of Jones' reagent. The mixture is poured into ice/water and extracted with ether which has been washed neutral with water. After drying over magnesium sulphate and concentration, there are obtained 10.9 g of a yellow oil which is chromatographed on a 100-fold amount of silica gel with toluene/ethyl acetate. By crystallization of the corresponding fractions from methylene chloride/ether there is obtained pure 5-oxo-1,5-seco-A-trinor-17α-pregnane-21,17-carbolactone of melting point 134°–135° C.; $[\alpha]_D = +7°$ (dioxan, c=0.2).

The 1,5-seco-A-trinorandrostane-5,17-dione 5-(ethylene acetal) used as the starting material is prepared as follows:

17β-Tert.butoxy-1,5-seco-A-trinorandrost-9-en-5-one is converted by reductive methylation into 17β-tert.butoxy-1,5-seco-A-trinorandrostan-5-one of melting point 128°–129° C. (from ether/hexane).

The resulting tert.butyl ether is cleaved with acetic acid/perchloric acid. Subsequent saponification with potassium carbonate in methanol gives 17β-hydroxy-1,5-seco-A-trinorandrostan-5-one of melting point 99°–100° C. (from ether/hexane).

Ketalization yields 17β-hydroxy-1,5-seco-A-trinorandrostan-5-one ethylene acetal of melting point 168°–169° C. (from ether/hexane).

After oxidation with pyridinium chlorochromate, there is obtained 1,5-seco-A-trinorandrostane-5,17-dione-5-(ethylene acetal) of melting point 140°–141° C. (from methylene chloride/hexane).

EXAMPLE 42

In a manner analogous to that described in Example 39, from 5-oxo-1,5-seco-A-trinor-17α-pregn-6-ene-21,17-carbolactone there is obtained 17β-hydroxy-17-(3-hydroxypropyl)-1,5-seco-A-trinorandrost-6-en-5-one of melting point 169°–171° (from acetone); $[\alpha]_D^{25} = -90°$ (dioxan, c=1).

EXAMPLE 43

2.5 g of 5-oxo-1,5-seco-A-trinor-17α-pregn-6-ene-21,17-carbolactone and 14.77 g of triphenylmethylphosphonium bromide are dissolved in 50 ml of dimethyl sulphoxide and the solution is treated at room temperature under argon within 10 minutes with a solution of 4.64 g of potassium tert.butylate in 50 ml of dimethyl sulphoxide. After 15 minutes, the mixture is adjusted to pH 2 to 3 with 6N hydrochloric acid while cooling and is then stirred for 30 minutes. The mixture is subsequently poured on to ice and extracted with ether which has been washed neutral with sodium chloride solution. After drying over magnesium sulphate and evaporation, there are obtained 11 g of a yellow oil which is chromatographed on 500 g of silica gel with toluene/ethyl acetate (19:1). There are thus obtained 650 mg of 1,2-seco-A-dinor-17α-pregna-2,6-diene-21,17-carbolactone which is crystallized from methanol; melting point 175°–176° C.; UV: $\lambda_{max} = 232$ nm, $\epsilon = 22000$; $[\alpha]_D = -64°$ (dioxan, c=0.2).

EXAMPLE 44

5-Oxo-1,5-seco-A-trinor-17α-pregn-9(11)-ene-21,17-carbolactone [melting point 150°–151.5° C. (from methylene chloride/ether); $[\alpha]_D = -40°$ (dioxan, c=0.5)] is obtained from 1,5-seco-A-trinorandrost-9(11)-ene-5,17-dione 5-(ethylene acetal) in an analogous manner to that described in Example 41.

The 1,5-seco-A-trinorandrost-9(11)-ene-5,17-dione 5-(ethylene acetal) used as the starting material is prepared as follows:

17β-Tert.butoxy-1,5-seco-A-trinorandrost-9-en-5-one is methylated in tert.butanol with potassium tert.butylate and methyl iodide. Depending on the conditions used there can be obtained as the main product either 17β-tert.butoxy-1,5-seco-A-trinorandrost-9(11)-en-5-one [melting point 118° C. (from methylene chloride/ether)] or 17β-tert.butoxy-6α-methyl-1,5-seco-A-trinorandrost-9(11)-en-5-one [melting point 147°–148° C. (from methylene chloride/ether)].

Cleavage of the tert.butyl ether with acetic acid/perchloric acid and subsequent saponification with potassium carbonate in methanol gives 17β-hydroxy-1,5-seco-A-trinorandrost-9(11)-en-5-one of melting point 119°–120° C. (from acetone/hexane).

Ketalization and subsequent oxidation with pyridinium chlorochromate yields 1,5-seco-A-trinorandrost-9(11)-ene-5,17-dione 5-(ethylene acetal) of melting point 171°–173° C. (from methylene chloride/acetone).

EXAMPLE 45

In a manner analogous to that described in Example 41, from 6α-methyl-1,5-seco-A-trinorandrostane-5,17-dione 5-(ethylene acetal) there is obtained 6α-methyl-5-oxo-1,5-seco-A-trinor-17α-pregnane-21,17-carbolactone of melting point 187°–188° C. (from methylene chloride/hexane); $[\alpha]_D = +3°$ (dioxan, c=0.5).

The 6α-methyl-1,5-seco-A-trinorandrostane-5,17-dione 5-(ethylene acetal) used as the starting material is prepared as follows:

17β-Tert.butoxy-1,5-seco-A-trinorandrostan-5-one is methylated with lithium diisopropylamide/methyl iodide. There is obtained 17β-tert.butoxy-6α-methyl-1,5-seco-A-trinorandrostan-5-one of melting point 140°–141° C.

Cleavage of the tert.butyl ether with acetic acid/perchloric acid and subsequent saponification gives 17β-hydroxy-6α-methyl-1,5-seco-A-trinorandrostan-5-one (melting point 124°–125° C.) from which there is obtained by ketalization 17β-hydroxy-6α-methyl-1,5-seco-A-trinorandrostan-5-one ethylene acetal of melting point 192°–193° C.

By oxidation with Jones' reagent there is finally obtained 6α-methyl-1,5-seco-A-trinorandrostane-5,17-dione 5-(ethylene acetal).

EXAMPLE 46

In a manner analogous to that described in Example 41, from 6α-methyl-1,5-seco-A-trinorandrost-9(11)-ene-5,17-dione 5-(ethylene acetal) there is obtained 6α-methyl-5-oxo-1,5-seco-A-trinorpregn-9(11)-ene-21,17-carbolactone of melting point 173°–175° C. (from methylene chloride/ether); $[\alpha]_D = -41°$ (dioxan, c=0.5).

The 6α-methyl-1,5-seco-A-trinorandrost-9(11)-ene-5,17-dione 5-(ethylene acetal) used as the starting material is prepared as follows:

From 17β-tert.butoxy-6α-methyl-1,5-seco-A-trinorandrost-9(11)-en-5-one there is obtained by cleavage of the tert.butyl ether with acetic acid/perchloric acid and subsequent saponification with methanolic potassium hydroxide solution 17β-hydroxy-6α-methyl-1,5-seco-A-trinorandrost-9(11)-en-5-one (melting point 90°–92° C.) from which there is obtained by ketalization 17β-hydroxy-6α-methyl-1,5-seco-A-trinorandrost-9(11)-en-5-one ethylene acetal of melting point 180°–182° C.

Oxidation with Jones' reagent yields 6α-methyl-1,5-seco-A-trinorandrost-9(11)-ene-5,17-dione 5-(ethylene acetal) of melting point 128°–129° C.

EXAMPLE 47

In a manner analogous to that described in Example 1, from 5-oxo-1,5-seco-D-homo-A-trinor-17aξ-pregnane-21,17a-carbolactone there is obtained 5-oxo-1,5-seco-D-homo-A-trinor-17aξ-pregn-6-ene-21,17a-carbolactone (isomer A) [melting point 227°–228° C. (from acetone/hexane); UV: $\lambda_{max}=229$ nm, $\epsilon=9300$; $[\alpha]_D = -113°$ (dioxan, c=0.2)] as well as, as a by-product, 6-bromo-5-oxo-1,5-seco-D-homo-A-trinor-17aξ-pregn-6-ene-21,17a-carbolactone (isomer A) m.p. 230°–234° (dec.)

From the corresponding isomer B there is obtained 5-oxo-1,5-seco-D-homo-A-trinor-17aξ-pregn-6-ene-21,17a-carbolactone (isomer B) [melting point 167°–168° C. (from acetone/hexane); UV: $\lambda_{max}=229$ nm, $\epsilon=9900$; $[\alpha]_D = -92°$ (dioxan, c=0.2)] as well as, as a byproduct, 6-bromo-5-oxo-1,5-seco-D-homo-A-trinor-17aξ-pregn-6-ene-21,17a-carbolactone (isomer B); melting point 190°–191° C. (from acetone/hexane); UV: $\lambda_{max}=254$ nm, $\epsilon=7800$; $[\alpha]_D = -10°$ (dioxan, c=0.2).

The 5-oxo-1,5-seco-D-homo-A-trinor-17aξ-pregnane-21,17a-carbolactone used as the starting material is prepared as follows:

1,5-Seco-A-trinorandrostane-5,17-dione 5-(ethylene acetal) is reacted with trimethylsulphonium methoxysulphate and potassium tert.butylate in dimethylformamide to give spiro[oxirane-2,17'(beta 1)-[1,5]seco-A-trinorandrostan]-5'-one ethylene acetal of melting point 131°–134° C. (from methanol).

Reaction with ammonia gives 17-(aminomethyl)-5,5-(ethylenedioxy)-1,5-seco-A-trinorandrostan-17β-ol [melting point 193°–196° C. (crude product)] from which by Tiffencan-Demjanow ring-expansion there is obtained 1,5-seco-A-trinor-D-homoandrostane-5,17a-dione 5-(ethylene acetal) of melting point 137°–138° C. (from acetone/hexane).

Therefrom there are obtained by a lithium Grignard reaction with 3-bromopropionaldehyde dimethyl acetal, cleavage of the two acetals with aqueous acetic acid and oxidation with Jones' reagent the two diastereomers of 5-oxo-1,5-seco-D-homo-A-trinor-17aξ-pregnane-21,17a-carbolactone having the following characteristics:

Isomer A, melting point 200.5°–201° C. (from acetone/hexane); $[\alpha]_D = +28°$ (dioxan, c=0.5).

Isomer B, melting point 222°–223° C. (from acetone/hexane); $[\alpha]_D = +24°$ (dioxan, c=0.5).

EXAMPLE 48

5 g of 5β-hydroxy-6,6-dimethyl-1,5-seco-A-trinorandrost-9(11)-en-17-one are dissolved in 100 ml of tetrahydrofuran and 1.25 g of lithium wire pieces are added to the solution under argon. Then, 21.5 g of 3-bromopropionaldehyde dimethyl acetal are added dropwise at ca −25° C. within 2 hours. After completion of the addition, the mixture is stirred for a further 1 hour at this temperature. The cooling bath is then removed and the mixture is again stirred for 1 hour, the temperature rising to 20° C. Working-up in the usual manner yields 8.4 g of an oil which is processed directly.

The whole of the crude product thus-obtained (8.4 g) is dissolved in 30 ml of glacial acetic acid and 12.7 ml of water are added. The mixture is left to stand overnight and is then worked-up. 6.9 g of crude product are obtained.

The whole of the crude product obtained is dissolved in 40 ml of acetone and oxidized at room temperature with 10 ml of Jones' reagent. The crude product (7.1 g) is chromatographed on 700 g of silicon dioxide with toluene/ethyl acetate. The corresponding fractions are pooled and crystallized from acetone/hexane. There is thus obtained pure 6,6-dimethyl-5-oxo-1,5-seco-A-trinor-17α-pregn-9(11)-ene-21,17-carbolactone of melting point 139°–141° C.; [α]$_D$= −109° (dioxan, c=0.15).

The 5β-hydroxy-6,6-dimethyl-1,5-seco-A-trinorandrost-9(11)-en-17-one used as the starting material is prepared as follows:

17β-Tert.butoxy-6α-methyl-1,5-seco-A-trinorandrost-9(11)-en-5-one is methylated with lithium diisopropylamide/methyl iodide to give 17β-tert.butoxy-6,6-dimethyl-1,5-seco-A-trinorandrost-9(11)-en-5-one of melting point 93.5°–95.5° C.

Lithium aluminium hydride reduction yields 17β-tert.butoxy-6,6-dimethyl-1,5-seco-A-trinorandrost-9(11)-en-5β-ol of melting point 163°–164° C.

Acetylation with pyridine/acetic anhydride at an elevated temperature yields 17β-tert.butoxy-6,6-dimethyl-1,5-seco-A-trinorandrost-9(11)-en-5β-ol acetate of melting point 129°–130° C.

Cleavage of the tert.butyl ether with acetic acid/perchloric acid and subsequent saponification with potassium carbonate in methanol gives 5β-acetoxy-6,6-dimethyl-1,5-seco-A-trinorandrost-9(11)-en-17β-ol of melting point 134°–135° C.

Oxidation with Jones' reagent gives 5β-acetoxy-6,6-dimethyl-1,5-seco-A-trinorandrost-9(11)-en-17-one (melting point 135.5°–136° C.) which is saponified by boiling in methanolic potassium hydroxide to give 5β-hydroxy-6,6-dimethyl-1,5-seco-A-trinorandrost-9(11)-en-17-one of melting point 175°–175.5° C.

EXAMPLE 49

In a manner analogous to that described in Example 36, from 6,6-dimethyl-5-oxo-1,5-seco-A-trinor-17α-pregn-9(11)-ene-21,17-carbolactone there is obtained potassium 17-hydroxy-6,6-dimethyl-5-oxo-1,5-seco-A-trinor-17α-pregn-9(11)-ene-21-carboxylate of melting point 261°–263° C.; [α]$_D$= −67° (ethanol, c=0.5).

EXAMPLE 50

In a manner analogous to that described in Example 48, from 5β-hydroxy-6,6-dimethyl-1,5-seco-A-trinorandrostan-17-one there is obtained 6,6-dimethyl-5-oxo-1,5-seco-A-trinor-17α-pregnane-21,17-carbolactone of melting point 126°–129° C. (from acetone/hexane); [α]$_D$= −58° (dioxan, c=0.2).

The 5-hydroxy-6,6-dimethyl-1,5-seco-A-trinorandrostan-17-one used as the starting material is prepared as follows:

17β-Tert.butoxy-6α-methyl-1,5-seco-A-trinorandrostan-5-one is methylated with lithium diisopropylamide/methyl iodide to give 17β-tert.butoxy-6,6-dimethyl-1,5-seco-A-trinorandrostan-5-one of melting point 123°–124° C.

Reduction of the 5-ketone with sodium borohydride and subsequent acetylation yields 5β-acetoxy-17β-tert.butoxy-6,6-dimethyl-1,5-seco-A-trinorandrostane of melting point 117°–118° C.

Cleavage of the tert.butyl ether and subsequent treatment with potassium carbonate in methanol gives 5β-acetoxy-6,6-dimethyl-1,5-seco-A-trinorandrostan-17β-ol of melting point 149°–151° C.

Oxidation with Jones' reagent gives 5β-acetoxy-6,6-dimethyl-1,5-seco-A-trinorandrostan-17-one (melting point 132°–133° C.) from which there is obtained by saponification 5β-hydroxy-6,6-dimethyl-1,5-seco-A-trinorandrostan-17-one of melting point 183°–184° C.

EXAMPLE 51

In a manner analogous to that described in Example 48, from 6,6-dimethyl-5-oxo-1,5-seco-A-trinor-17α-pregnane-21,17-carbolactone there is obtained potassium 17-hydroxy-6,6-dimethyl-5-oxo-1,5-seco-A-trinor-17α-pregnane-21-carboxylate of melting point 274°–284° C. (from isopropanol); [α]$_D$= −38° (methanol, c=0.5).

The following Examples illustrate pharmaceutical preparations containing the deA-steroids provided by the present invention:

EXAMPLE A

A tablet for oral administration can contain the following ingredients:

| | |
|---|---|
| Active ingredient (e.g. 5-oxo-A-tetranor-17α-pregna-9,11-diene-21,17-carbolactone) | 25 mg |
| Maize starch | 100 mg |
| Lactose | 50 mg |
| Polyvinylpyrrolidone | 15 mg |
| Magnesium stearate | 2 mg |

EXAMPLE B

A capsule for oral administration can contain the following ingredients:

| | |
|---|---|
| Active ingredient (e.g. 5-oxo-A-tetranor-17α-pregna-9,11-diene-21,17-carbolactone) | 25 mg |
| Maize starch | 125 mg |
| Lactose | 125 mg |

What is claimed is:

1. A compound of a formula selected from the group consisting of

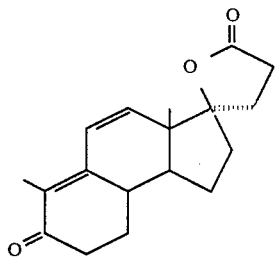

and

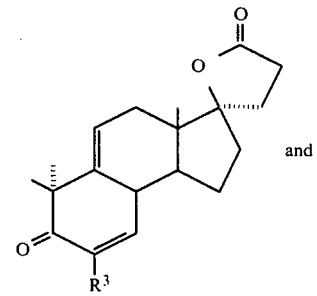

-continued

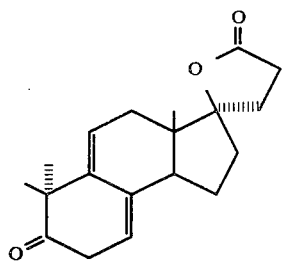

wherein $R^3$ is hydrogen or methyl.

2. The compound in accordance with claim 1, 5-oxo-1,5-seco-A-trinor-17α-pregna-6,9(11)-diene-21,17-carbolactone.

3. The compound in accordance with claim 1, 5-oxo-1,5-seco-A-trinor-17α-pregna-7,9(11)-diene-21,17-carbolactone.

4. The compound in accordance with claim 1, 6-methyl-5-oxo-1,5-seco-A-trinor-17α-pregna-6,9(11)-diene-21,17-carbolactone.

5. The compound in accordance with claim 1, 5-oxo-A-tetranor-17α-pregna-9,11-diene-21,17-carbolactone.

* * * * *